(12) United States Patent
Beyerlein

(10) Patent No.: US 8,574,195 B2
(45) Date of Patent: *Nov. 5, 2013

(54) SYSTEMS AND METHODS FOR DETECTING TISSUE CONTACT AND NEEDLE PENETRATION DEPTH USING STATIC FLUID PRESSURE MEASUREMENTS

(75) Inventor: Dagmar Beyerlein, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1521 days.

This patent is subject to a terminal disclaimer.

(21) Appl. No.: 10/656,491

(22) Filed: Sep. 5, 2003

(65) Prior Publication Data

US 2004/0260240 A1  Dec. 23, 2004

Related U.S. Application Data

(63) Continuation-in-part of application No. 10/166,854, filed on Jun. 10, 2002.

(51) Int. Cl.
 *A61M 1/00* (2006.01)
(52) U.S. Cl.
 USPC .......................................................... 604/118
(58) Field of Classification Search
 USPC ......... 604/117, 118, 505, 246, 264, 275, 121, 604/187, 272, 274; 600/300
 See application file for complete search history.

(56) References Cited

U.S. PATENT DOCUMENTS

| 2,001,638 | A |   | 5/1935 | Tornsjo |
| 2,646,042 | A | * | 7/1953 | Hsi Hu Quang ................ 604/38 |
| 4,186,750 | A |   | 2/1980 | Patel |
| 4,299,230 | A | * | 11/1981 | Kubota ......................... 600/300 |
| 4,356,826 | A |   | 11/1982 | Kubota |
| 4,411,657 | A | * | 10/1983 | Galindo ....................... 604/274 |
| 4,964,854 | A |   | 10/1990 | Luther |
| 5,279,567 | A |   | 1/1994 | Ciaglia et al. |

(Continued)

FOREIGN PATENT DOCUMENTS

| DE | 44 20 232 A1 | 12/1995 |
| DE | 4420 231 A1 | 12/1995 |

OTHER PUBLICATIONS

Chapter 1 PCT International Preliminary Report (IPER) for PCT Application No. PCT/US2004/027961. Mailed on Mar. 16, 2006 (9 pages).

(Continued)

*Primary Examiner* — Bhisma Mehta
*Assistant Examiner* — Bradley Osinski
(74) *Attorney, Agent, or Firm* — Angela M. Augustus; Blakely Sokoloff Taylor & Zafman LLP

(57) ABSTRACT

Systems and methods for determining tissue contact and penetration depth are provided. In one aspect, the system includes a needle and a pressure measurement assembly. The needle, in one exemplary embodiment, includes a first end and a second end with at least one aperture located a predetermined distance from the first end. The fluid pressure measurement assembly is connected with a portion of the needle to measure pressure of fluid dispensed in the needle. The fluid pressure measurement assembly measures a first pressure of the fluid, a second pressure when the needle contacts tissue and a third pressure when the needle penetrates the tissue and the aperture becomes occluded.

16 Claims, 16 Drawing Sheets

(56) References Cited

U.S. PATENT DOCUMENTS

| | | | |
|---|---|---|---|
| 5,292,309 A * | 3/1994 | Van Tassel et al. | 604/117 |
| 5,396,897 A * | 3/1995 | Jain et al. | 600/561 |
| 5,419,777 A | 5/1995 | Hofling | |
| 5,421,821 A | 6/1995 | Janicki et al. | |
| 5,425,376 A | 6/1995 | Banys et al. | |
| 5,454,791 A | 10/1995 | Tovey et al. | |
| 5,470,316 A | 11/1995 | Tovey | |
| 5,496,273 A | 3/1996 | Pastrone et al. | |
| 5,551,427 A | 9/1996 | Altman | |
| 5,571,133 A | 11/1996 | Yoon | |
| 5,649,911 A | 7/1997 | Trerotola | |
| 5,656,339 A | 8/1997 | Wesseling | |
| 5,662,107 A * | 9/1997 | Sakariassen | 600/369 |
| 5,746,713 A * | 5/1998 | Hood et al. | 604/22 |
| 5,800,395 A * | 9/1998 | Botich et al. | 604/110 |
| 5,817,074 A * | 10/1998 | Racz | 604/272 |
| 5,871,495 A | 2/1999 | Mueller | |
| 5,873,366 A | 2/1999 | Chim et al. | |
| 5,878,751 A | 3/1999 | Hussei et al. | |
| 5,928,943 A | 7/1999 | Franz et al. | |
| 5,941,868 A | 8/1999 | Kaplan et al. | |
| 5,954,701 A | 9/1999 | Matalon | |
| 5,964,757 A | 10/1999 | Ponzi | |
| 6,030,377 A | 2/2000 | Linhares et al. | |
| 6,102,887 A | 8/2000 | Altman et al. | |
| 6,102,926 A | 8/2000 | Tartaglia et al. | |
| 6,162,202 A * | 12/2000 | Sicurelli et al. | 604/272 |
| 6,217,554 B1 | 4/2001 | Green | |
| 6,248,112 B1 * | 6/2001 | Gambale et al. | 606/108 |
| 6,251,079 B1 | 6/2001 | Gambale et al. | |
| 6,254,573 B1 | 7/2001 | Haim et al. | |
| 6,254,598 B1 | 7/2001 | Edwards et al. | |
| 6,283,951 B1 * | 9/2001 | Flaherty et al. | 604/529 |
| 6,302,870 B1 | 10/2001 | Jacobsen et al. | |
| 6,309,370 B1 | 10/2001 | Haim et al. | |
| 6,391,005 B1 | 5/2002 | Lum | |
| 6,494,862 B1 | 12/2002 | Ray et al. | |
| 6,517,521 B1 | 2/2003 | Ly | |
| 6,546,787 B1 | 4/2003 | Schiller et al. | |
| 6,620,139 B1 | 9/2003 | Plicchi et al. | |
| 6,905,476 B2 | 6/2005 | Ponzi | |
| 7,094,201 B1 | 8/2006 | Stokes et al. | |
| 2002/0072706 A1 | 6/2002 | Hiblar et al. | |
| 2003/0083686 A1 * | 5/2003 | Freeman et al. | 606/181 |
| 2004/0092893 A1 | 5/2004 | Haider et al. | |
| 2004/0171933 A1 * | 9/2004 | Stoller et al. | 600/427 |
| 2005/0027199 A1 * | 2/2005 | Clarke | 600/473 |

OTHER PUBLICATIONS

Abbott Cardiovascular Systems, Non-final Office Action mailed Mar. 28, 2011 for U.S. Appl. No. 10/869,691., 13 pages.
Advanced Cardiovascular Systems, Final office action dated Jun. 20, 2011 for U.S. Appl. No. 10/869,691.
Abbott Cardiovascular Systems, Non final office action dated Jul. 6, 2010 for U.S. Appl. No. 10/869,691.
Abbott Cardiovascular Systems, Final office action mailed Nov. 9, 2010 for U.S. Appl. No. 10/869,691.
Abbott Cardiovascular Systems, Non final office action dated Jun. 24, 2009 for U.S. Appl. No. 10/869,691.
Abbott Cardiovascular Systems, Final office action dated Dec. 8, 2009 for U.S. Appl. No. 10/869,691.

* cited by examiner

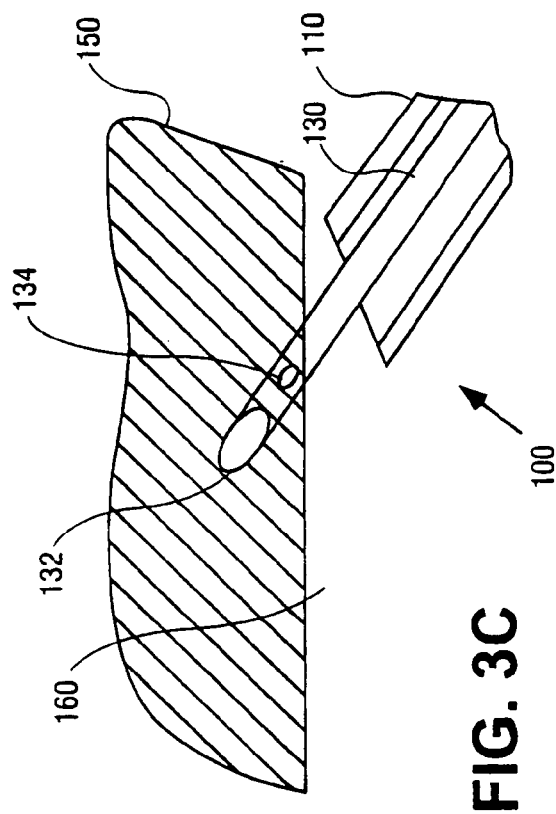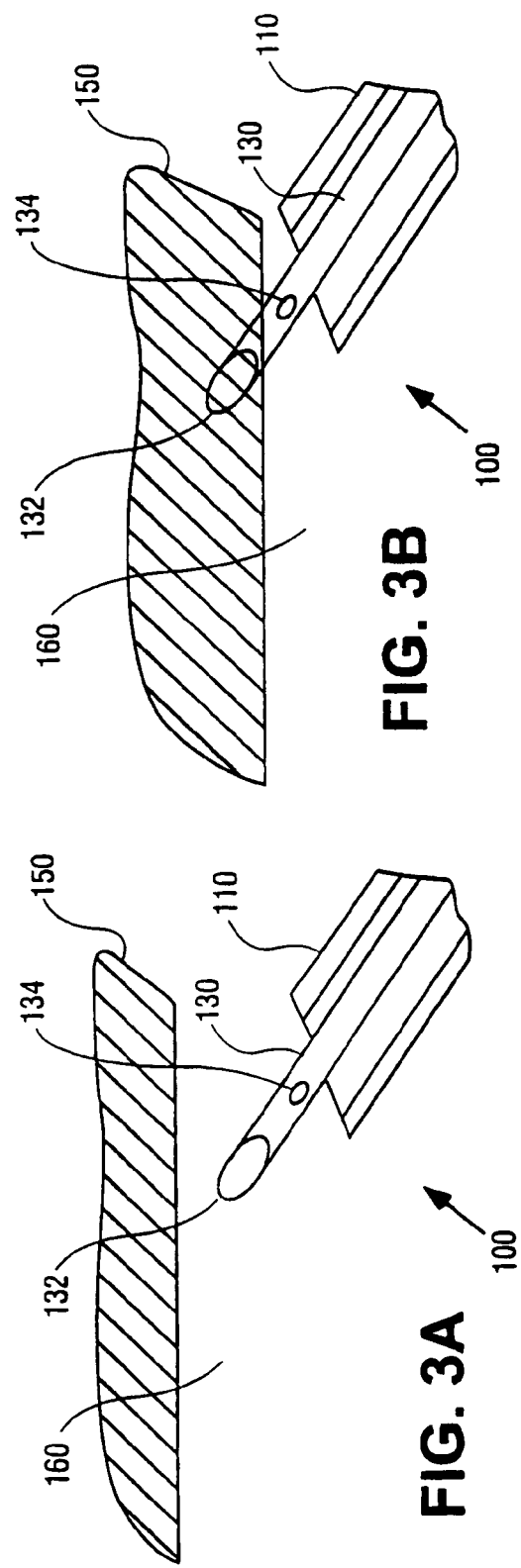

Fluid Injection Pressure
Saline, 0.002" Aperture 1 mm Proximal to Needle Tip

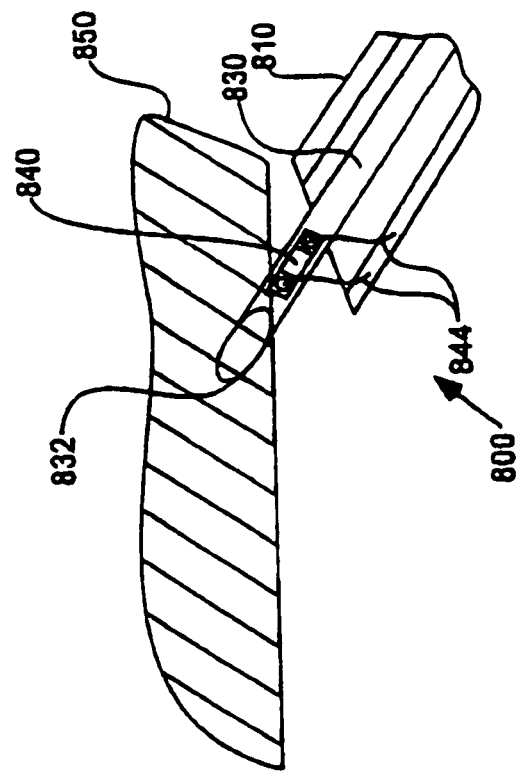
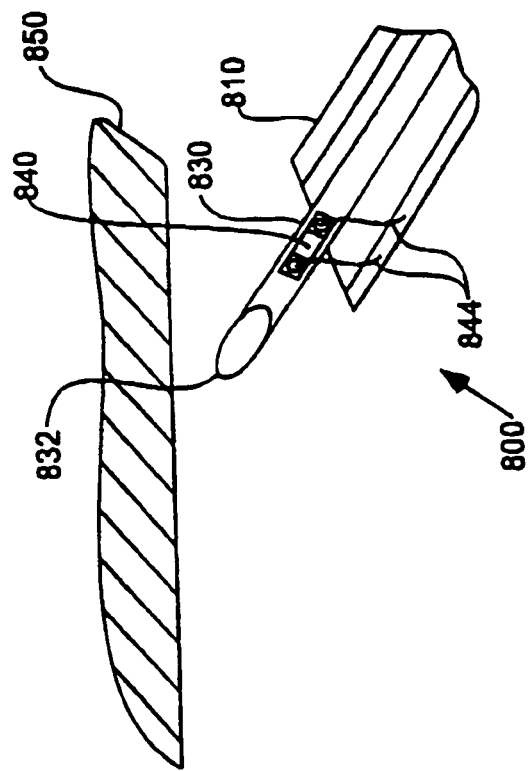

US 8,574,195 B2

SYSTEMS AND METHODS FOR DETECTING TISSUE CONTACT AND NEEDLE PENETRATION DEPTH USING STATIC FLUID PRESSURE MEASUREMENTS

RELATED APPLICATION

This is a continuation in part of U.S. patent application Ser. No. 10/166,854, filed on Jun. 10, 2002. The application Ser. No. 10/166,854 is hereby incorporated by reference in its entirety.

FIELD

The invention relates generally to needles, and more particularly, to a system and method for detecting tissue contact and needle penetration depth.

BACKGROUND

Drug delivery systems currently exist that supply therapeutic substances through a needle to regions of a patient's body. Such regions may include a diseased blood vessel, body cavity or organ. In the case of a diseased blood vessel, for example, the therapeutic agent may be used to treat an arterial lesion and/or to promote an angiogenic response In some applications, a needle may be connected to a catheter assembly to deliver the therapeutic agent deep into the body. In this application, it is often difficult to determine when the needle contacts the organ, cavity wall, or vessel wall. Further, it is difficult to determine the penetration depth of the needle. In many of the applications for which a needle catheter assembly is used to deliver therapeutic agents to regions within the body, the agent must be delivered to a precise location. Accordingly, it is described to provide feedback that indicates when the needle contacts the cavity or vessel wall and when the needle has been inserted to a predetermined depth.

SUMMARY

Systems and methods for determining tissue contact and penetration depth are provided. In one aspect, the system includes a needle and a fluid pressure measurement assembly. The needle, in one exemplary embodiment, includes a first end and a second end with at least one aperture located a predetermined distance from the first end. The fluid pressure measurement assembly is connected with a portion of the needle to measure pressure of fluid dispensed in the needle. The fluid pressure measurement assembly measures a first pressure with the fluid dispensed in the needle, a second pressure when the needle contacts the tissue and begins to compress the fluid in the needle and a third pressure when the needle penetrates the tissue further compressing the fluid in the needle, and the aperture becomes occluded.

In an alternative aspect, the system includes a needle and a fluid pressure sensor. The fluid pressure sensor, in another exemplary embodiment, is coupled with a portion of the needle. The needle, in one exemplary embodiment, includes a first end and a second end with at least one aperture located a predetermined distance from the first end. The sensor is connected with a portion of the needle to allow for measurement of pressure of fluid dispensed in the needle. The sensor allows for measurement of a first pressure with the fluid dispensed in the needle, a second pressure when the needle contacts the tissue and begins to compress the fluid in the needle and a third pressure when the needle penetrates the tissue further compressing the fluid in the needle, and the aperture becomes occluded. The fluid pressure sensor is located a predetermined distance from the first end of the needle.

BRIEF DESCRIPTION OF THE DRAWINGS

The present invention is illustrated by way of example, and not limitation, in the figures of the accompanying drawings in which:

FIGS. 3a-3c illustrate the embodiment of the fluid delivery catheter of FIG. 1 in different positions with respect to the tissue;

FIGS. 10a and 10b illustrate the embodiment of the fluid delivery catheter of FIG. 10 in different positions with respect to the tissue;

DETAILED DESCRIPTION

Systems and methods for detecting tissue contact and needle penetration depth are described. In the following detailed description of the present invention, numerous specific details are set forth in order to provide a thorough understanding of the present invention. However, it will be apparent to one skilled in the art that the present invention may be practiced without these specific details. In some instances, well-known structures and devices are shown in block diagram form, rather than in detail, in order to avoid obscuring the present invention. Several exemplary embodiments are described herein, and it will be appreciated that alternative embodiments exist within the scope of this invention.

Figure 1:
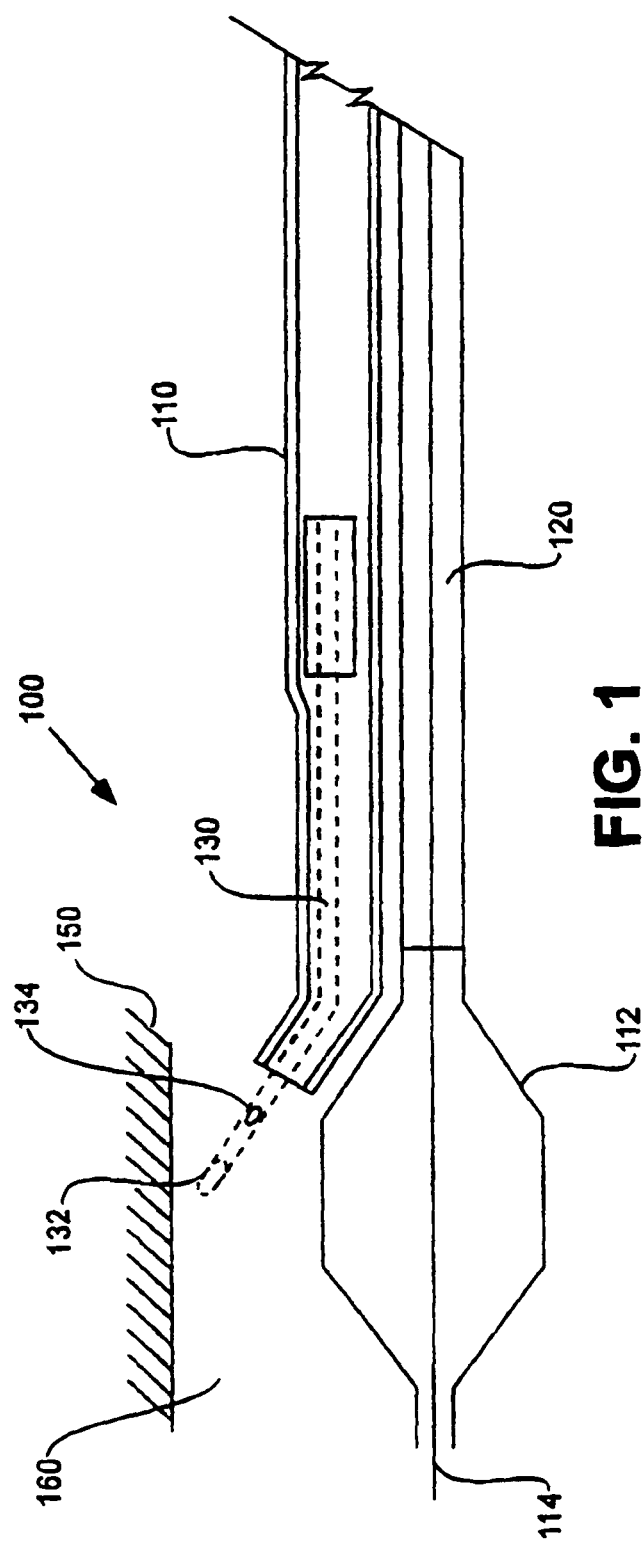
FIG. 1 illustrates a side cross-sectional view of one embodiment of a fluid delivery catheter.

FIG. 1 illustrates a side cross sectional view of one embodiment of a fluid delivery catheter 100. The fluid delivery catheter 100 can be used to provide therapeutic agents to a particular region of a patient's body, for example, to prevent or treat arterial disease (e.g. arterial stenosis or restenosis). The fluid delivery catheter 100 can be any medical device designed for insertion into a region of a patient's body to permit injection of fluids. It is contemplated that the fluid delivery catheter has applicability for use with any region within a patient's body, including blood vessels (e.g. coronary arteries), blood vessel wall, cardiac muscle, urinary tract, intestinal tract, kidney ducts, and other sites.

In FIG. 1, the fluid delivery catheter 100 includes a needle 130 within a needle sheath 110. The needle sheath is mounted on a dilatation catheter 120. The fluid delivery catheter 100 is shown within a cavity 160 of a patient's body in FIG. 1. The cavity 160 may be a lumen of a blood vessel, such as a coronary artery, or cardiac tissue. The fluid delivery catheter 100 is maneuvered over a guidewire 114. The guidewire directs the fluid delivery catheter 100 through torturous passageways within the body to arrive at the desired body cavity 160. The dilatation catheter 120 has a balloon 112 that inflates and directs the needle tip 132, which is extendable, toward body tissue such as a blood vessel wall 150.

Figure 2:
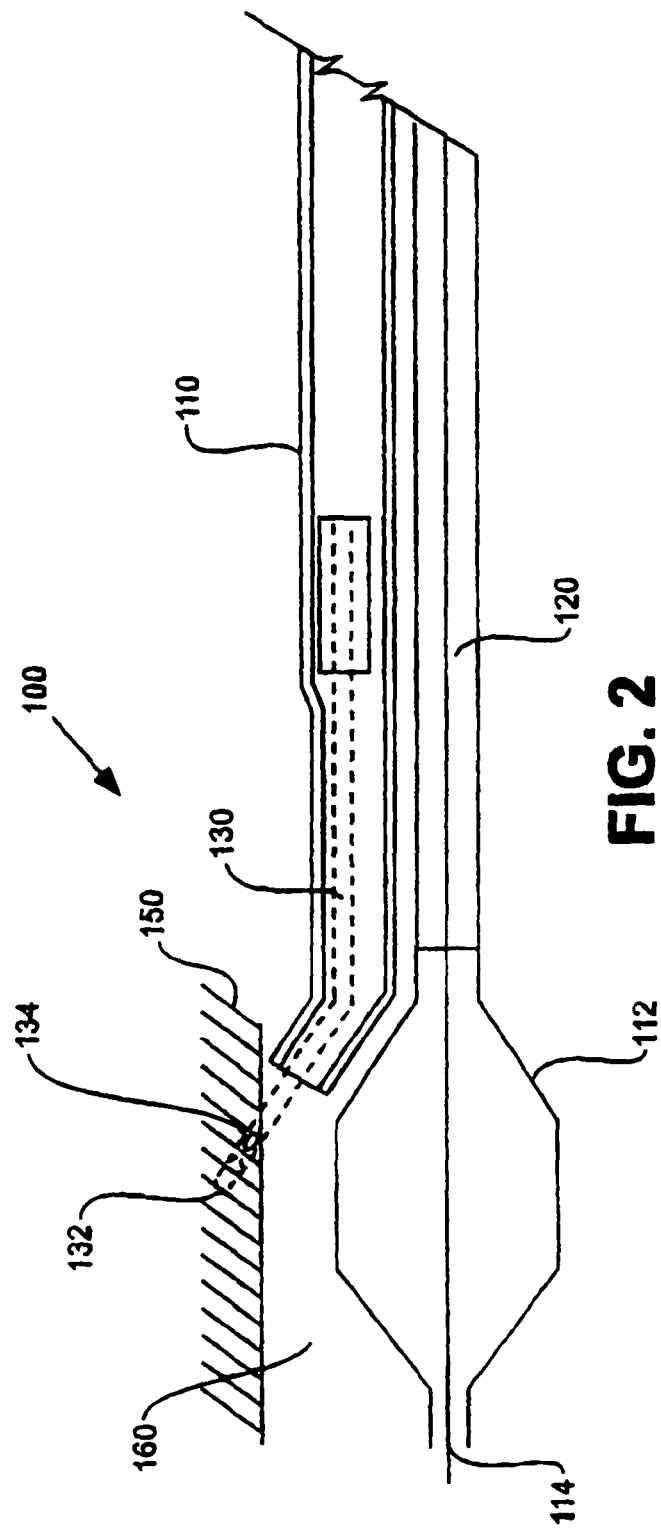
FIG. 2 illustrates the embodiment of the fluid delivery catheter of FIG. 1 where the needle penetrates tissue.

The needle 130 includes a needle tip 132 and an aperture 134 located a predetermined distance from the needle tip 132. As the needle 130 is inserted into body tissue, first the needle tip 132 lumen and then the aperture 134 become occluded. This is shown in FIG. 2. The occlusion of the needle tip 132 lumen and aperture 134 increase the injection pressure of the fluid within the needle 130, thereby allowing an operator to determine tissue contact and penetration depth of the needle 130.

In one embodiment, the fluid is constantly flowing through the needle 130 as the needle 130 is being advanced into the body tissue. The dynamic injection pressure of the fluid is measured. With the fluid constantly flowing through the needle 130, the fluid dynamic injection pressure changes (increases) as the needle tip 132 lumen contacts the body tissue, and changes (increases) again when the aperture 134 becomes occluded. The changes in the fluid dynamic injection pressure indicate the changes in the penetration depth of the needle 130.

In another embodiment, the fluid is dispensed into the needle 130 but not constantly flowing through the needle 130 as the needle 130 is being advanced into the body tissue. The static pressure of the fluid is measured. With the fluid dispensed in the needle 130, a first static pressure is measured. As the needle tip 132 lumen contacts the body tissue, the tissue compresses the fluid within the needle and the static pressure changes (increases) resulting in a second static pressure measurement. As the needle 130 penetrates deeper into the body tissue and the aperture 134 becomes occluded, the static pressure changes (increases) resulting in a third static pressure measurement. The changes in the static fluid pressure (from the first, to second and to the third pressure) indicate the changes in the penetration depth of the needle 130.

In one embodiment the needle 130 may include more than one aperture 134 spaced in predetermined distances from the needle tip new number of the needle 130. For example, a first aperture 134 may be located a first predetermined distance from the needle tip 132. A second aperture (not shown) may be located a second predetermined distance from the first aperture 134. In alternative embodiments, there may be more than two apertures.

In one embodiment, the space between the apertures may be the same. In other alternative embodiments, the distances between the apertures may be different. In another embodiment, the apertures may all be the same size and shape while in another embodiment the sizes and shapes of the apertures could be different. The apertures should be much smaller than the needle tip 132 lumen so that the fluid will be ejected from the needle tip 132 lumen rather than the aperture 134. In one embodiment, the occlusion of both the needle tip 132 lumen and individual aperture 134 and the concomitant increases of fluid pressure allow an operator to determine the penetration depth of the needle 130 as it becomes embedded in the vessel wall 150. The fluid pressure includes the dynamic pressure and the static pressure of the fluid depending on the embodiments. In embodiments where the fluid is constantly flowing through the needle 130 as the needle 130 is advanced into the body tissue, the pressure changes indicate the changes in the dynamic injection pressure of the fluid. In embodiments where the fluid is dispensed through the needle 130 prior to the injection and the fluid is static (e.g., not flowing) through the needle 130 as the needle 130 is advanced into the body tissue, the pressure changes indicate the changes in the static pressure of the fluid as the tissue compresses the fluid in the needle 130. The changes the static fluid pressure or the injection dynamic pressure allow an operator to determine the penetration depth of the needle 130 as it becomes embedded in the vessel wall 150.

FIG. 2 illustrates the embodiment of the fluid delivery catheter 100 of FIG. 1 where the needle 130 is shown penetrating a vessel wall 150. As the needle tip 132 contacts the vessel wall 150, the needle tip 132 lumen becomes occluded. Then, as the needle 130 further penetrates the vessel wall 150, the aperture 134 that is located a predetermined distance from the needle tip 132 becomes occluded. Accordingly, in alternative embodiments, the predetermined distance between the needle tip 132 and aperture 134 may vary according to what the desired penetration depth may be.

In one embodiment, injection pressure measurements are taken continuously as a therapeutic agent is injected from the first end of a needle, through the needle 130, and through the needle tip 132 lumen. The pressure measurements indicate the dynamic injection pressures of the therapeutic agent as the needle 130 is advancing into the tissue. The changes in the dynamic injection pressure indicate the penetration depth of the needle 130.

In an alternative embodiment, a first static fluid pressure is measured when the needle 130 is filled with a therapeutic agent; a second static fluid pressure is measured when the needle tip 132 contacts the vessel wall 150 and as the needle tip 132 lumen becomes occluded; and a third static fluid pressure is measured when the needle 130 advances further into the vessel wall 150 and the aperture 134 becomes occluded. The therapeutic agent is not injected continuously as the needle 130 is being advanced. The pressure measurements indicate the static fluid pressure of the therapeutic agent as the needle 130 is advancing into the tissue. The changes in the static pressure caused by the compression of the fluid by the tissue indicate the penetration depth of the needle 130.

As the vessel wall or other tissue within the body occludes the needle tip 132 lumen, an increase in pressure will occur. Accordingly, an operator is able to determine by the increase in fluid pressure that the needle tip 132 has contacted the vessel wall. As the vessel wall or other tissue occludes the aperture 134, another increase in fluid pressure will occur. An operator is again able to determine by the second increase in pressure that the needle 130 has been inserted to a predetermined depth in the tissue or vessel wall 150.

Figure 2A:
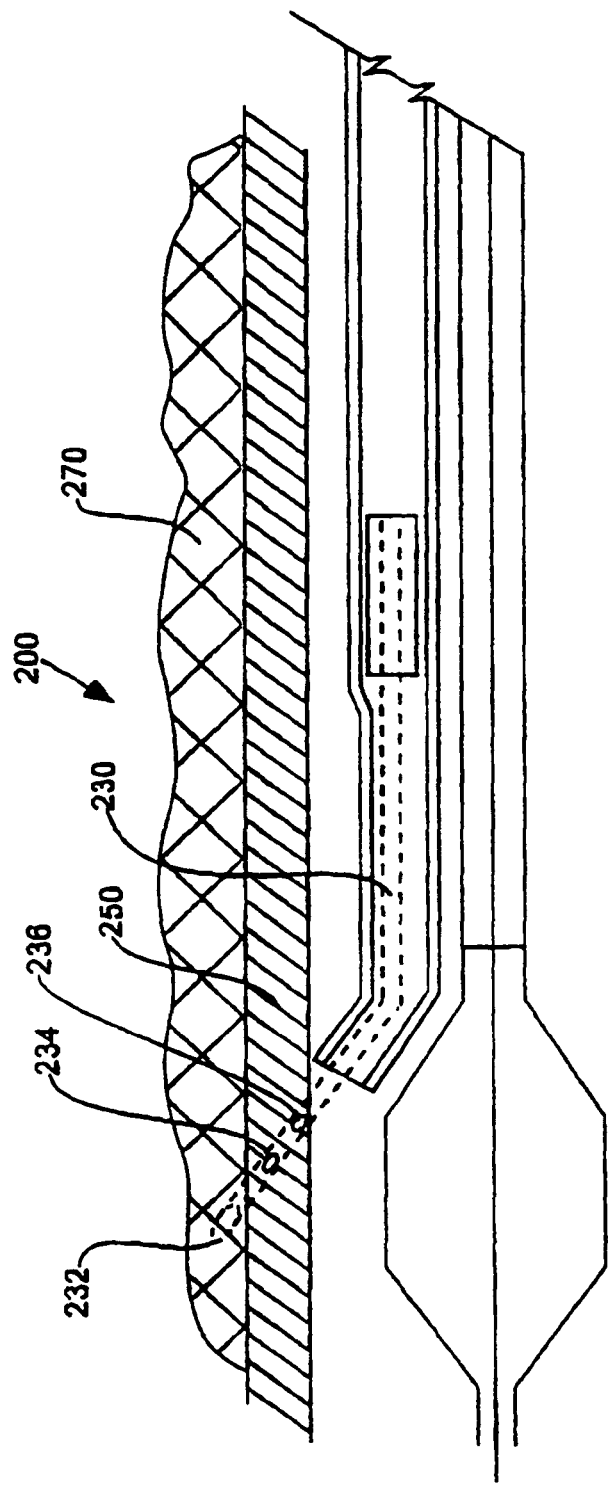
FIG. 2a illustrates an alternative embodiment of a fluid delivery catheter where a needle penetrates and extends into tissue beyond the vessel wall.

FIG. 2A illustrates an alternative embodiment of a fluid delivery catheter 200 where a needle 230 penetrates and extends into tissue 270 beyond the vessel wall 250. In FIG. 2A, the needle 230 includes more than one aperture. The first aperture 234 is located a predetermined distance from the needle tip 232 so that occlusion of the first aperture 234 indicates penetration of the needle 230 a certain depth into the first tissue layer or vessel wall 250. The second aperture 236 is located a predetermined distance from the first aperture 234 so that the occlusion of the second aperture 236 indicates a further penetration of the needle 230. In some cases, an operator may have knowledge about the thickness of certain tissue. For example, the vessel wall 250 may be a known thickness. The second aperture 236 may then be placed according to that known thickness so that occlusion of the second aperture 236 indicates the needle 230 has penetrated all the way through the first layer of tissue 250 and into the second layer of tissue 270.

FIGS. 3A-3C illustrate an embodiment of the fluid delivery catheter 100 in different positions with respect to the vessel wall 150. FIG. 3A illustrates the fluid delivery catheter 100 where the needle 130 has not yet contacted the vessel wall 150. The needle tip 132 is close to and proximate to but not contacting the vessel wall 150. In one embodiment, a therapeutic agent is dispensed in the needle 130 prior to the penetration of the needle 130 into the vessel wall 150. The therapeutic agent is not continuously injected through the needle 130 as the needle 130 is being advanced in this embodiment. As shown in FIG. 3A, the needle 130 has not yet contacted the vessel wall 150. The initial pressure of therapeutic agent can be taken to indicate the first static fluid pressure.

FIG. 3B illustrates the fluid delivery catheter 100 where a portion of the needle tip 132 lumen is contacting and has become embedded in the vessel wall 150. However, the needle 130 has not been fully inserted into the vessel 150. Accordingly, as seen in FIG. 3B, the desired penetration depth of the needle 130 has not been achieved. In the embodiment where the therapeutic agent is dispensed in the needle 130 prior to the penetration of the needle 130 into the vessel wall 150 and not continuously being injected through the needle 130 as the needle 130 is being advanced, as the needle tip 132 lumen contacts and becomes embedded in the vessel wall 150, the tissue compresses the fluid and the static fluid pressure increases to a second static fluid pressure. The increase in the static fluid pressure indicates to the operator that the needle tip 132 lumen has penetrated the vessel wall 150 but that the desired penetration depth has not been achieved.

FIG. 3C illustrates the fluid delivery catheter 100 where the needle 130 has penetrated the vessel wall 150 to a predetermined depth. The desired penetration depth has been achieved when the vessel wall 150 tissue occludes the aperture 134. As seen in FIG. 3C, both the needle tip 132 lumen and the aperture 134 are embedded within the vessel wall 150. Accordingly, as discussed above, an operator is able to determine by the increase in static fluid pressure caused by the occlusion of the aperture 134 that the needle 130 has penetrated the tissue to a predetermined depth. In the embodiment where the therapeutic agent is dispensed in the needle 130 prior to the penetration of the needle 130 into the vessel wall 150 and not continuously being injected through the needle 130 as the needle 130 is being advanced, as the aperture 134 contacts and becomes embedded in the vessel wall 150, the static fluid pressure increases to a third static fluid pressure. The increase in the static fluid pressure indicates to the operator that the needle tip 132 lumen has penetrated the vessel wall 150 and the aperture 134 has become occluded and that the desired penetration depth has been achieved.

Figure 4:
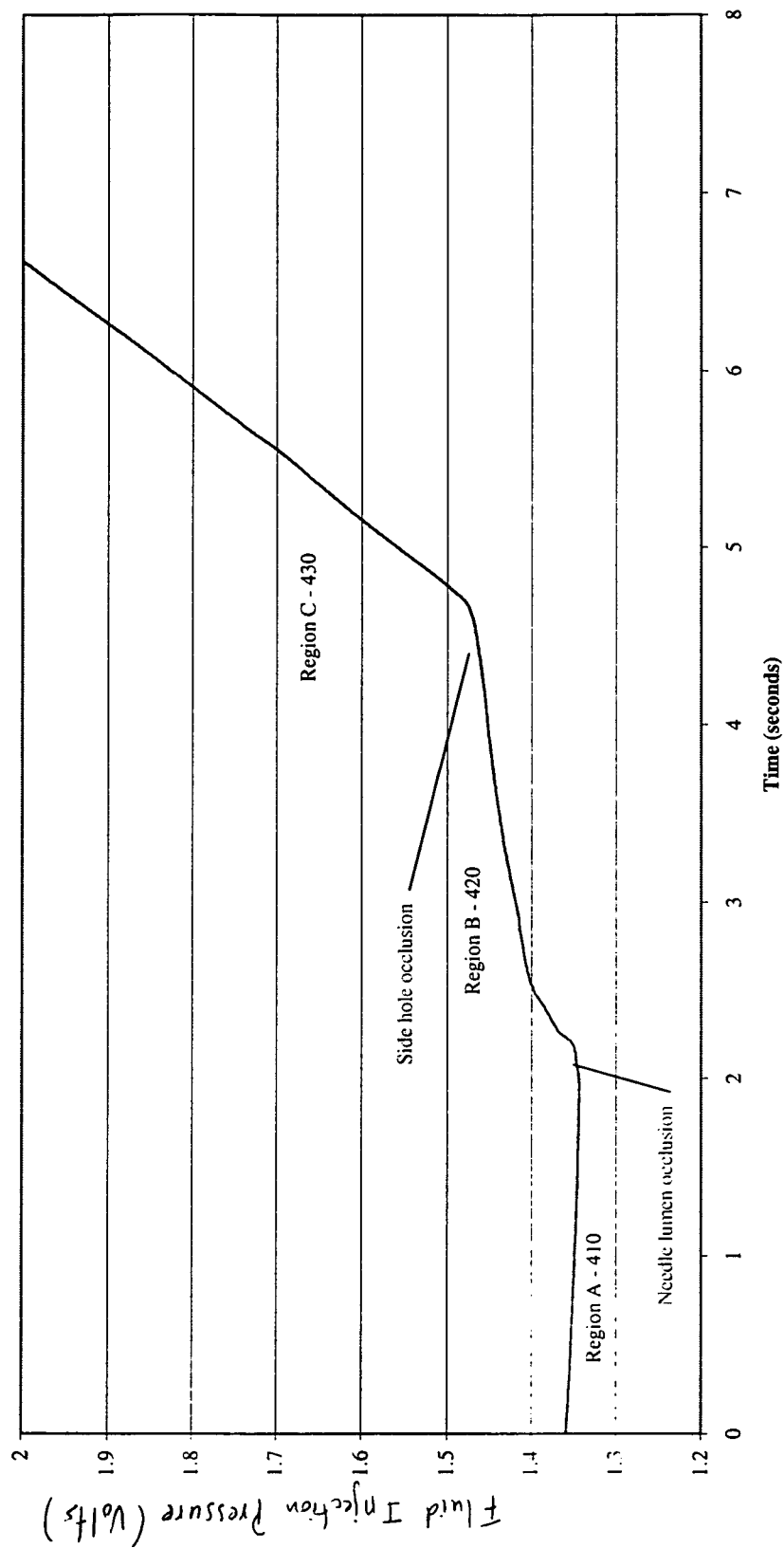
FIG. 4 illustrates a graph representing different fluid injection pressure measurements within the needle corresponding to various positions of the needle with respect to the tissue as shown in FIGS. 3a-3c where the fluid is constantly being injected through the needle as it is being advanced.

FIG. 4 illustrates a graph representing different pressure measurements of fluid within the needle 130 taken at the three needle positions shown in FIG. 3A through 3C. In one embodiment, the pressure measurements are dynamic measurements of injection pressure. A therapeutic agent is continuously and constantly injected through the needle 130 as the needle 130 is being advanced into the vessel wall 150. The graph is representative of pressure versus time where it is assumed that the needle 130 is pushed into vessel wall 150 over time in the sequence shown in FIGS. 3A (first), 3B (next), and 3C (last). As the needle 130 is in the body cavity 160 as seen in FIG. 3A but not contacting the vessel wall 150, the injection pressure is lower than the scenarios shown in FIGS. 3B and 3C. This pressure measurement is shown as region A 410 in FIG. 4. As a portion of the needle tip 132 penetrates the vessel wall 150, an increase in dynamic injection pressure occurs. The pressure increases dramatically after the needle tip lumen 132 becomes occluded, but the rate decreases slightly shortly thereafter as shown in region B 420 in FIG. 4. As the needle 130 penetrates the tissue or the vessel wall 150 a predetermined depth and the aperture 134 becomes occluded, a second dramatic increase in injection pressure is detected. This pressure spike is shown as region C 430 in FIG. 4. Although only 3 points are shown in FIG. 4 corresponding to FIGS. 3A 3B and 3C, if additional apertures were to be added on the needle, additional pressure increases would occur as each aperture became occluded.

Figure 5:
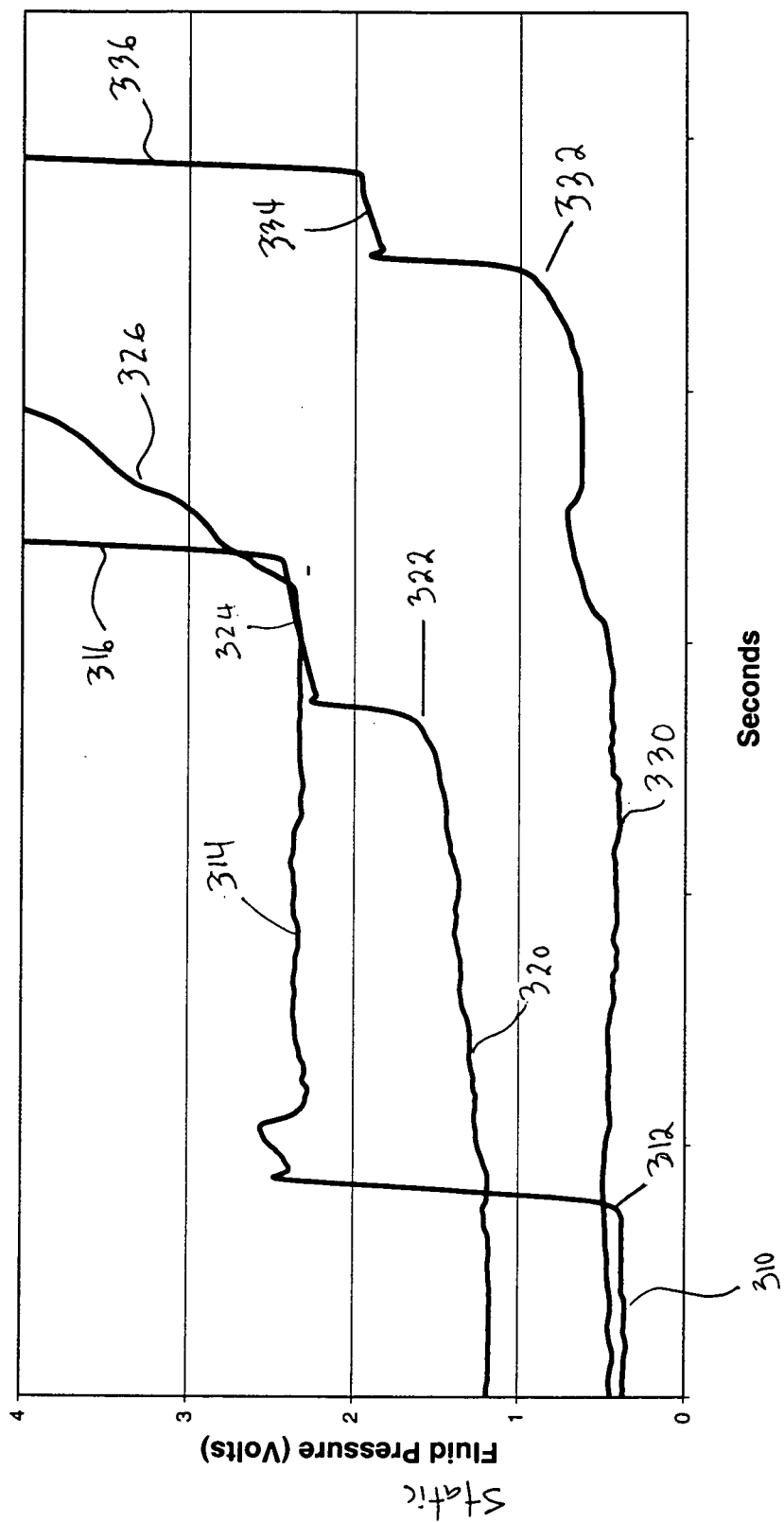
FIG. 5 illustrates a graph representing different static fluid pressure measurements within the needle corresponding to various positions of the needle with respect to the tissue as shown in FIGS. 3a-3c where the fluid is static (e.g., not flowing) through the needle as it is being advanced.

FIG. 5 illustrates a graph representing different pressure measurements of fluid within the needle 130 taken at the three needle positions shown in FIG. 3A through 3C. In one embodiment, the pressure measurements are static fluid pressure measurements. The needle 130 is filled with a therapeutic agent but the therapeutic agent is not continuously injected through the needle 130. Three graphs are illustrated in FIG. 5, one for each time the needle 130 penetrates into the vessel wall 150. The therapeutic agent may be different each time. Alternatively, the vessel wall 150 may be of different types, for example, the vessel wall 150 may be a cardiac tissue. The vessel wall 150 may be any type of tissue.

In one embodiment, the graphs are representative of pressure versus time where it is assumed that the needle 130 is pushed into vessel wall 150 over time in the sequence shown in FIGS. 3A (first), 3B (next), and 3C (last). As the needle 130 is in the body cavity 160 as seen in FIG. 3A but not contacting the vessel wall 150, the static fluid pressure is lower than the scenarios shown in FIGS. 3B and 3C. This static fluid pressure measurement is shown as region 310, 320, or 330 in FIG. 5. As a portion of the needle tip 132 lumen penetrates the vessel wall 150, an increase in static fluid pressure occurs. The tissue from vessel wall 150 occludes the needle tip 132 lumen beginning with the needle tip 132 and compresses the therapeutic agent in the needle 130. The static fluid pressure increases dramatically after the needle tip 132 lumen becomes occluded as shown in region 312, 322, or 332. The rate decreases slightly shortly thereafter as shown in region 314, 324, or 334 in FIG. 5. As the needle 130 penetrates the tissue or the vessel wall 150 a predetermined depth and the aperture 134 becomes occluded, a second dramatic increase in static fluid pressure is detected. The tissue from the vessel wall 150 occludes the aperture 134 as well as the needle lumen thus exerting even more pressure on the therapeutic agent in the needle 130. This pressure spike is shown as region 316, 326, or 336 in FIG. 5. Although only 3 points are shown in FIG. 5, if additional apertures were to be added on the needle, additional pressure increases would occur as each aperture became occluded.

Figure 6:
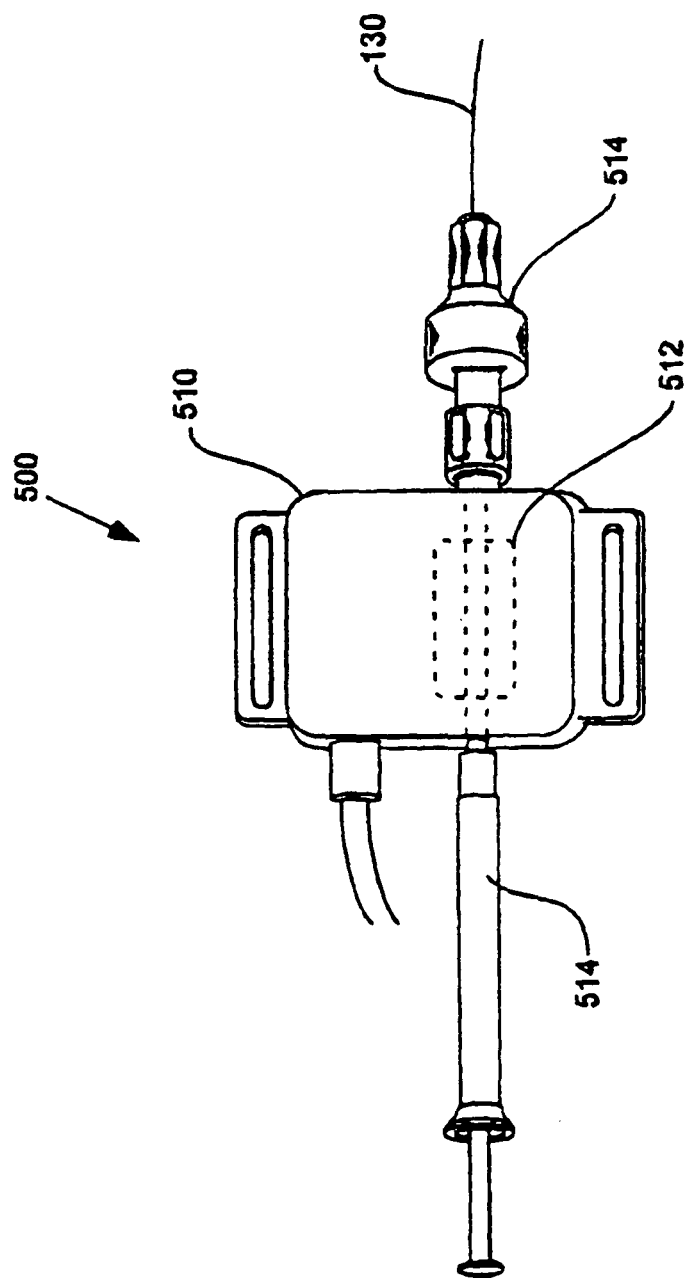
FIG. 6 illustrates a front view of one assembly for measuring the pressure of the fluid in the needle.

FIG. 6 illustrates a front view of one embodiment of a fluid pressure measurement assembly 500 connected to a needle 130. In one embodiment, as shown in FIG. 6, the fluid pressure measurement assembly 500 includes a sensor 512 to measure fluid pressure.

Figure 7:
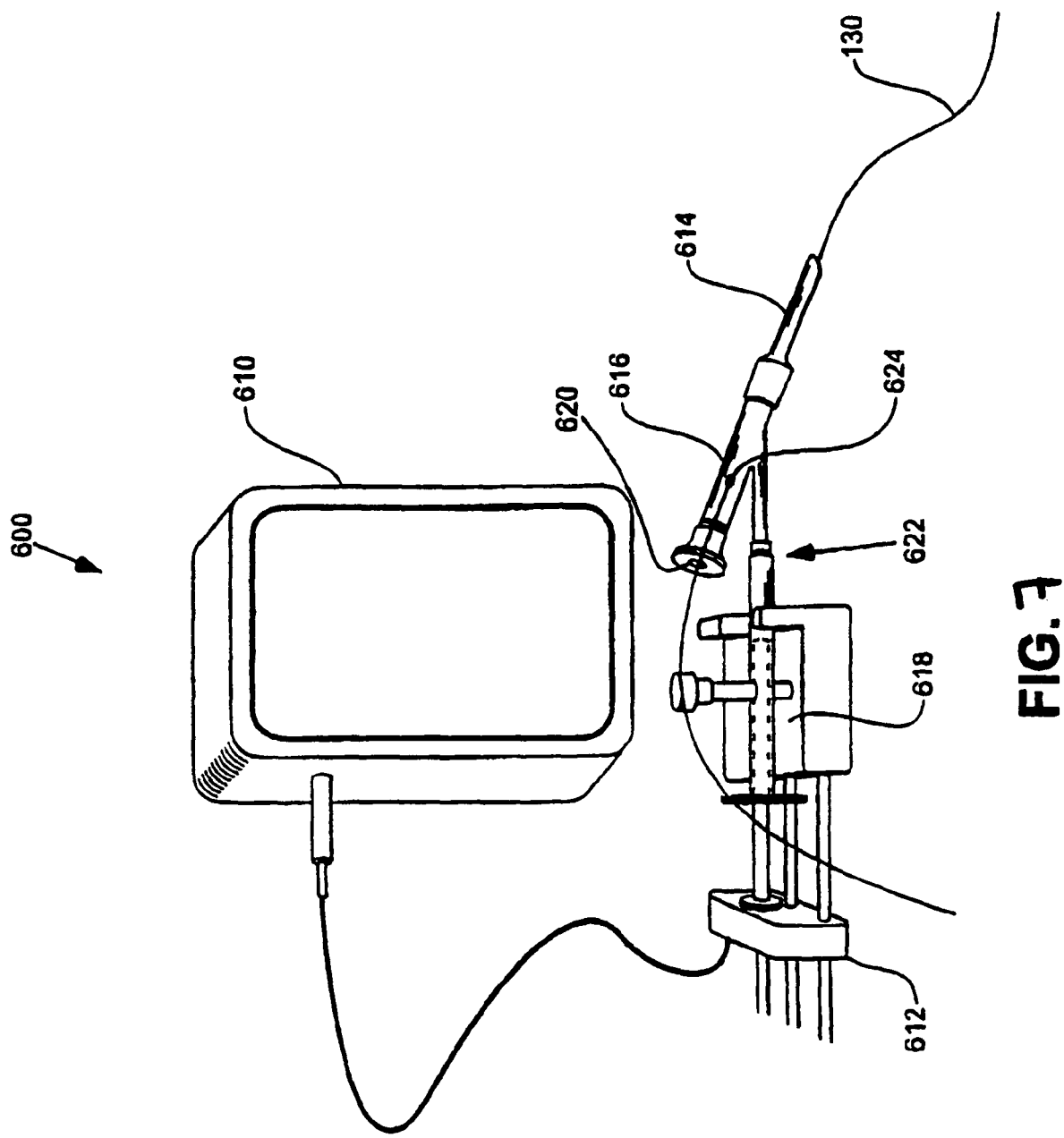
FIG. 7 illustrates a front view of an alternative assembly for measuring the pressure of the fluid in the needle.

As seen in FIG. 6, one end of the pressure measurement assembly 500 is connected to a syringe 514. In one embodiment, a syringe pump 612 in FIG. 7 is used to inject the fluid from the syringe 514 and through the needle 130 at a constant, controlled rate. In another embodiment, the syringe pump 612 is not necessary. The needle 130 may be filled with the fluid prior to use by any convenient method. In one embodiment, it is preferable to not have the fluid constantly being pumped through the needle 130.

In one embodiment, the sensor 512 detects a first fluid injection pressure increase as the needle tip contacts tissue. The sensor 512 measures a second fluid injection pressure increase as the needle 130 penetrates the tissue to a predetermined depth. The second fluid injection pressure increase occurs as the aperture in the needle (shown in FIGS. 1-3) becomes occluded, thereby increasing the fluid injection pressure of the therapeutic agent being injected into the tissue.

In another embodiment, the sensor 512 detects a first static fluid pressure of the fluid in the needle 130. The sensor 512 also detects a second static fluid pressure as the needle tip 132 lumen contacts the tissue. The sensor 512 also determines the static fluid pressure change between the first and the second static fluid pressure (an increase in pressure) to indicate that the needle tip 132 lumen has contacted the tissue and has become occluded. The sensor 512 further measures a third static fluid pressure as the needle 130 penetrates the tissue to a predetermined depth when the aperture 134 in the needle 130 (shown in FIGS. 1-3) becomes occluded. The sensor 512 also determines the static fluid pressure change between the second and third pressure (another increase in pressure) to indicate that the needle 130 has reached the predetermined depth. The fluid pressure increase occurs as the aperture as well as the needle lumen becomes occluded.

An example of a fluid pressure measurement assembly 500 that may be utilized with the present invention is a disposable fluid pressure monitoring system manufactured by Utah Medical Products, Inc. The assembly 500 may easily be attached to a luer lock attached to the proximal end of the needle 130. The disposable fluid pressure monitoring system provides fluid path visualization. Different manufacturers may also produce similar fluid pressure measurement systems that are capable of being utilized in the context of the present invention. Alternatively, a much smaller fluid pressure sensor assembly can be integrated directly into the needle assembly. For example, a smaller version of the sensor 512 could be mounted onto a small plastic connector that is used to attach the needle to the syringe.

Figure 8:
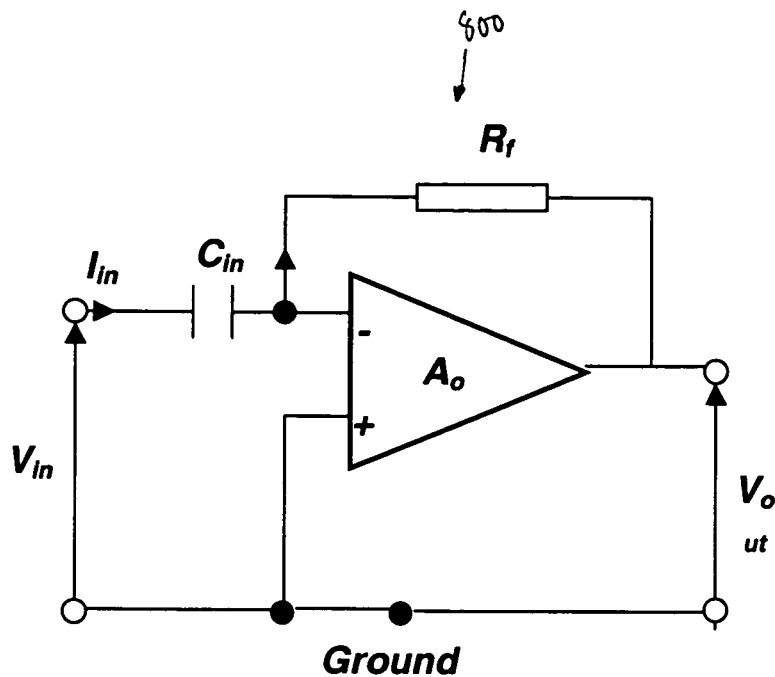
FIG. 8 illustrates an exemplary circuit scheme that can be incorporated into a pressure measuring assembly to measure changes in pressure.
Figure 9:
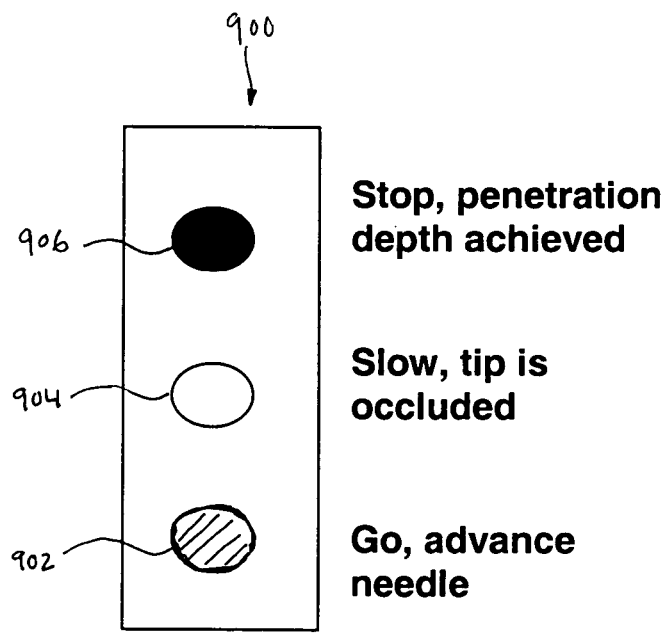
FIG. 9 illustrates a visual indicator that can be incorporated into a pressure measuring assembly to indicate the position of the needle.

In one embodiment, the fluid pressure measurement assembly 500 incorporates a visual feedback system such as the indicator 900 shown in FIG. 9 to allow the operator to monitor the penetration depth of the needle 130. A signal processor can be included for use with the visual feedback system. In one embodiment, the signal processor uses a differentiating amplifier 800 (shown in FIG. 8) to detect an increase in pressure (e.g., by using a transducer output voltage). The signal processor determines the initial pressure of the fluid dispensed in the needle 130 and determines the changes (or alternatively, rate of changes) in pressure caused by occlusion to the needle tip 132 lumen and/or the aperture 134. In one embodiment, the signal processor may cause the visual indicator 900 to show a window 902 to indicate that the needle 130 has not reached the tissue and to give the operator the "go" signal to advance the needle 130. The "go" signal may be indicated when the pressure of the fluid remains relatively the same as the initial pressure of the fluid. In other words, there is no significant change in the pressure of the fluid. The magnitude of the change in the pressure of the fluid may be predetermined as shown in FIGS. 4-5. Alternatively, the "go" signal may be indicated when there is no significant change in the rate of change of the fluid pressure. In one embodiment, when the magnitude of change in pressure, or alternatively, the rate of change in pressure, is insignificant, the signal processor causes the visual indicator 900 to show the window 902 to signal the operator to advance the needle 130.

Next, the signal processor may cause the visual indicator 900 to show a window 904 to indicate that the needle 130 has penetrated the tissue and the needle tip 132 lumen is occluded. The window 904 may be used to indicate that the change in the pressure of the fluid is significant and correlates to the penetration depth of the needle 130 where the needle tip 132 lumen is occluded by the tissue. The magnitude of the increase may be predetermined as shown in FIGS. 4-5. The magnitude of the increase in pressure as the needle tip 132 lumen is occluded is significantly larger than the magnitude of the increase in the pressure when the tissue has not occluded the lumen. Alternatively, the window 904 may be used to indicate that the rate of change in the pressure of the fluid is significant and correlates to the penetration depth of the needle 130 where the needle tip 132 lumen is occluded by the tissue. Based on an assessment of the magnitude of the increase in pressure, or alternatively, the rate of change in pressure, the signal processor may cause the window 904 to indicate to the operator to proceed with the advancement of the needle 130 slowly.

Next, the signal processor may cause the visual indicator 900 to show a window 906 to indicate that the needle 130 has penetrated the tissue to the predetermined distance and that the needle tip 132 lumen as well as the aperture 134 is occluded. The window 906 may be used to indicate that the change in the pressure of the fluid is dramatic or significant and correlates to the penetration depth of the needle 130 where the needle tip 132 lumen as well as the aperture 134 is occluded by the tissue. The magnitude of the increase may be predetermined as shown in FIGS. 4-5. The magnitude of the increase in pressure as the needle tip 132 lumen is occluded is significantly larger than the magnitude of the increase in the pressure when the tissue has occluded the needle tip 132 lumen. Alternatively, the window 906 may be used to indicate that the rate of change in the pressure of the fluid is dramatic or significant and correlates to the penetration depth of the needle 130 where the needle tip 132 lumen as well as the aperture 134 is occluded by the tissue. Based on an assessment of the magnitude of the increase in pressure, or alternatively, the rate of change in pressure, the signal processor may cause the window 906 to indicate to the operator to stop the advancement of the needle 130 because the penetration depth has been achieved.

In an alternative embodiment, an audible feedback system is incorporated into the pressure measurement assembly 500 instead of or in addition to the visual feedback system. The audible feedback system may be incorporated similarly to the visual feedback system previously described. Instead of having the visual indicator 900, the sensor 512 may incorporate a convenient audible feedback system. In one embodiment, the audible feedback system is recognizable by human such as a beeping sound. A slow beep may be used to indicate that the needle is filled with a fluid but has not reached the tissue. A faster beep may be used to indicate that the needle tip has penetrated the tissue and has become occluded. An even faster beep may be used to indicate that the needle 130 has reached the predetermined depth of the aperture and that the operator may stop.

In an alternative embodiment, a computer processor (not shown) is coupled to the pressure measurement assembly 500 to measure, calculate, and assess the change or rate of change in the fluid pressure (dynamic or static) in the needle 130. In one embodiment, the computer processor is configured to use the differential amplifier 800 shown in FIG. 8 to measure the rate of changes in pressure of the fluid dispensed in the needle 130. The computer processor is also configured to determine and distinguish the rate of changes in the pressure to determine and distinguish the various penetration depths of the needle 130. The computer processor is also coupled to the visual feedback system indicator 900 and/or the audible feedback system to issue various human-recognizable signals (e.g., visual indicator and audible indicator) to the operator as to the positions or penetration depths of the needle 130.

FIG. 7 illustrates a front view of an alternative embodiment of a pressure measurement assembly 600 connected to the proximal end of the needle 130. The pressure measurement assembly 600 includes a signal processor and pressure display 610. Here, a proximal end of a bifurcated connector 616 has a transducer port 620 and a connection port 622 that connects the bifurcated connector 616 to the syringe 618. The needle 130 is connected to a distal end of the bifurcated connector 616. The syringe 618 is placed on a syringe pump 612.

The syringe pump 612 pumps a therapeutic agent at a constant rate through the needle 130. The therapeutic agent should be pumped very slowly so that the amount of therapeutic agent that is dispensed before the needle reaches the desired penetration depth is minimized. As the needle 130 advances and its tip makes contact with or penetrates tissue, the occlusion of the needle tip creates a first resistance to the flow of the therapeutic agent. This is detected by the pressure sensor 624. Accordingly, the increase in pressure indicates that the needle 130 has contacted tissue.

The operator continues to advance the needle 130 until the tissue begins to occlude the aperture (shown in FIGS. 1-3) of the needle 130. As the aperture becomes fully occluded, this increases the resistance to the flow of the therapeutic agent and results in a second pressure increase as shown in region C in FIG. 4.

In an alternative embodiment, a handheld syringe 618 or another suitable device is used to dispense a therapeutic agent into the needle 130 prior to inserting the needle 130 into the patient. The initial static fluid pressure of the therapeutic agent is measured. As the needle 130 advances and its tip lumen makes contact with or penetrates tissue, the occlusion of the needle tip lumen creates an increase in the static fluid pressure of the therapeutic agent. This is detected by the pressure sensor 624. Accordingly, the increase in pressure indicates that the needle 130 has contacted tissue. The operator continues to advance the needle 130 until the tissue begins to occlude the aperture (shown in FIGS. 1-3) of the needle 130. As the aperture becomes fully occluded, the static fluid pressure of the therapeutic agent increases even more. In the embodiments where the aperture correlates to the desired penetration depth for the needle, the last increase in fluid pressure indicates that the needle 130 has reached the desired penetration depth.

Figure 10:
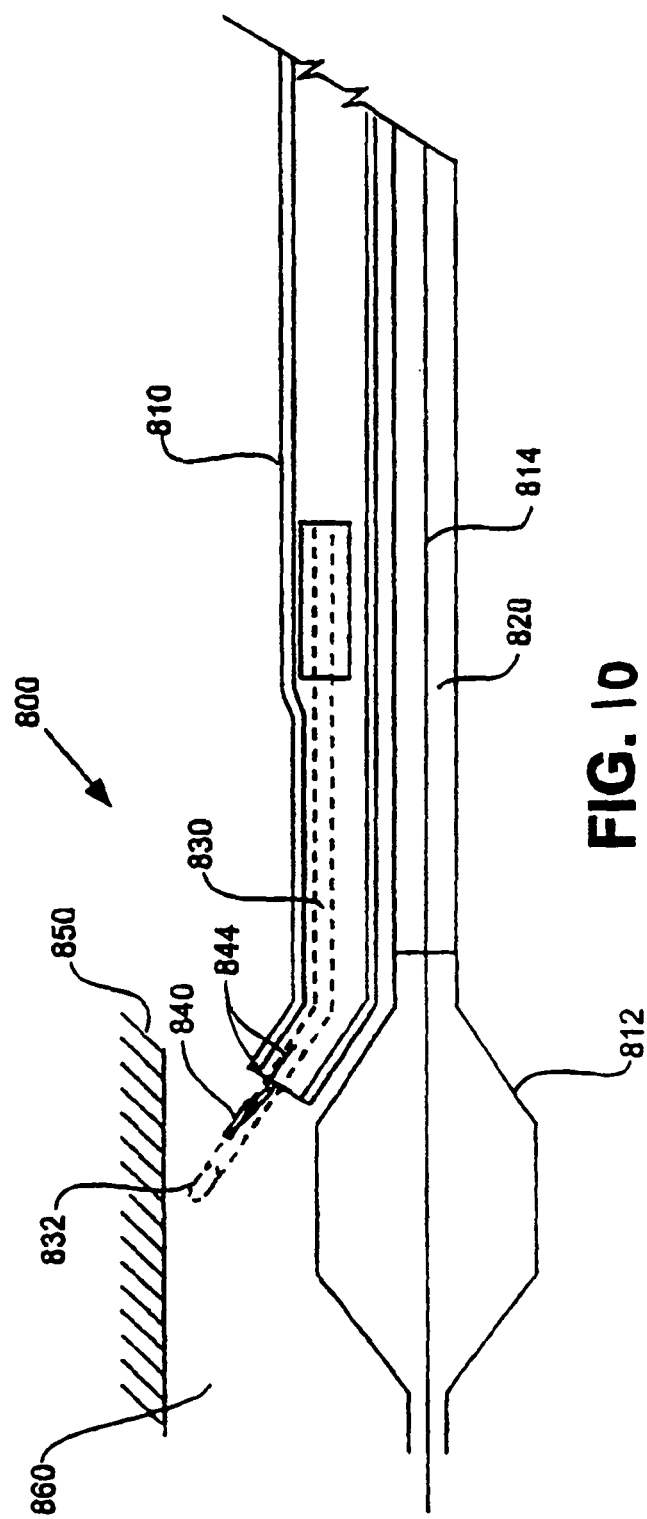
FIG. 10 illustrates a side cross-sectional view of an embodiment of a fluid delivery catheter with a force transducer.

FIG. 10 illustrates a side cross-sectional view of an alternative embodiment of a fluid delivery catheter 800 including an attached strain gauge 840. Similar to FIG. 1, the fluid delivery catheter 800 includes a needle 830 within a needle sheath 810. The needle sheath 810 is attached to a dilatation catheter 820. The dilatation catheter 820 is delivered into the body over a guidewire 814 that guides the dilatation catheter 820 through tortuous pathways within a patient's body to a desired region or body cavity 860. The dilatation catheter 820 may include a balloon 812 that inflates and directs the distal end of the needle sheath 810 and needle 830 toward a vessel wall 850. The operator pushes the needle 830 toward the vessel wall 850 so that a needle tip 832 contacts the vessel wall 850. The needle 830 continues to move into the vessel wall 850 until a predetermined depth is reached. Here, the predetermined depth is reached when the distal portion of the strain gauge 840 contacts the vessel wall 850. As shown in FIG. 7, the strain gauge 840 includes leads 844 extending from the strain gauge 840 to the proximal end of the needle.

An example of a strain gauge 840 that may be utilized with the present invention is a miniature semiconductor strain gauge manufactured by Entran. These strain gauges may be processed from P-type silicon in orientation, which provide maximum sensitivity to applied strain. Different strain gauges may also be available in other configurations. Different manufacturers may also produce similar strain gauges that are capable of being utilized in the present invention. In order to prevent false signals, the signal from the strain gauge should be offset or calibrated to the appropriate level of force that the tissue is expected to exert during successful tissue penetration. The force exerted by the tissue after successful needle penetration is much greater and longer in duration than accidental contact with the needle sheath, catheter assembly or vessel wall. To minimize false signals further, the force measurements should be taken only after the fluid delivery catheter 700 has reached its intended destination.

FIGS. 10A and 10B illustrate the embodiment of the fluid delivery catheter 800 of FIG. 10 in different positions with respect to the vessel wall 850. FIG. 10A illustrates the fluid delivery catheter 800 where the needle 830 has not yet contacted the vessel wall 850. The needle tip 832 is close to and proximate to but not contacting the vessel wall 850.

FIG. 10B illustrates the fluid delivery catheter 800 where a portion of the needle tip 832 is contacting and has become embedded in the vessel wall 850. The needle 830 is inserted a predetermined depth into the vessel wall 850. As seen in FIG. 7, the strain gauge 840 is attached to the needle 830 at a predetermined distance from the needle tip 832. When the needle 830 penetrates the vessel wall 850 to a predetermined depth, the strain gauge contacts the vessel wall 850 and senses contact pressure from the tissue. The contact pressure of the tissue thus signals to the operator that a certain penetration depth of the needle 830 has been achieved.

Figure 11:
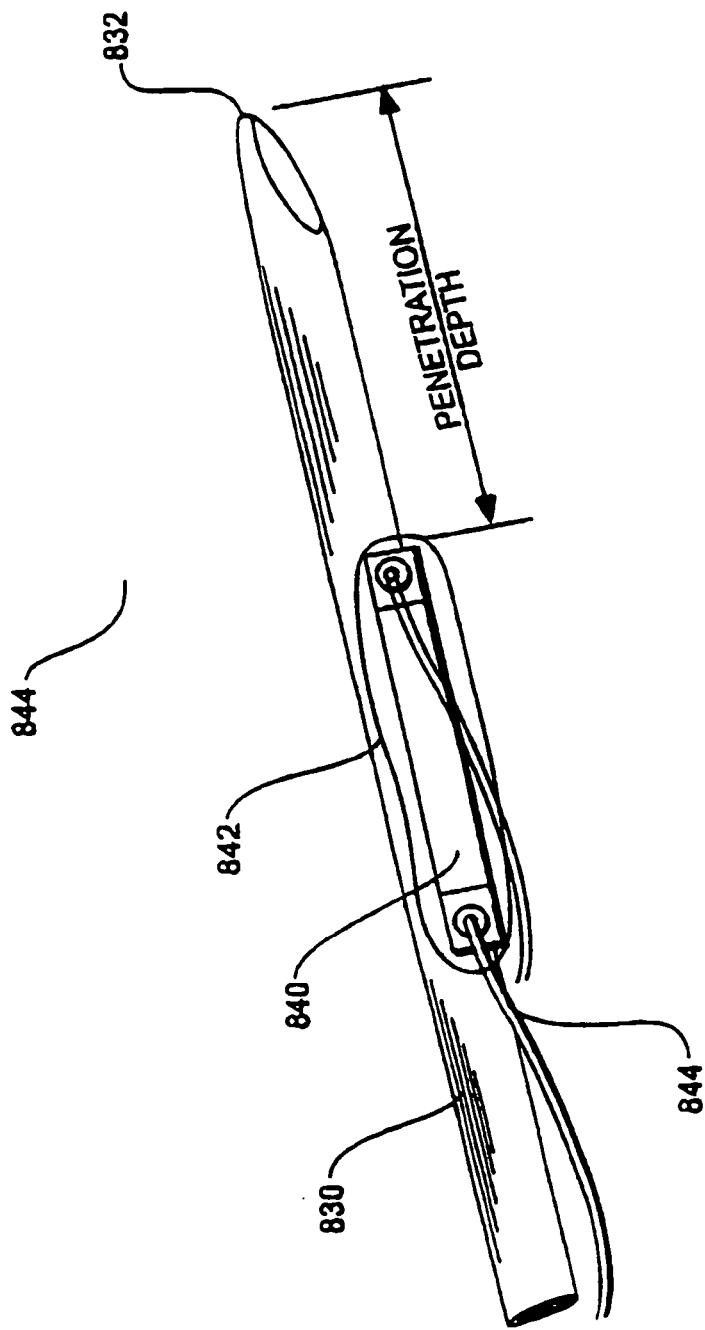
FIG. 11 illustrates an enlarged view of the embodiment of the needle and the force transducer shown in FIG. 10.

FIG. 11 illustrates an enlarged view of the embodiment of the needle 830 and strain gauge 840 shown in FIG. 10. The strain gauge 840 is shown attached to the needle 830 a predetermined distance from the needle tip 832. This allows the needle 830 to be inserted into the vessel wall or tissue to a predetermined penetration depth. In one embodiment, the predetermined depth is 0.5 to 3 millimeters. In one embodiment, as shown in FIG. 11, the strain gauge 840 is covered by an encapsulant 842 to protect the strain gauge 840.

Strain gauges are typically mounted very securely to the item that is expected to deform or experience strain. Since the needle 830 is relatively strong, it will not deform during tissue penetration and the securely mounted strain gauge 840 will not produce a signal. In one embodiment, the strain gauge is embedded in a soft polymeric encapsulant 842 before it is mounted on the needle 830. When the soft encapsulant 842 makes contact with tissue during penetration, it deforms and transfers this energy to the strain gauge 840. In one embodiment, the soft polymeric material encapsulant 842 may be made of silicone. In alternative embodiments, the encapsulant 842 may be made of other biocompatible materials.

Figure 12:
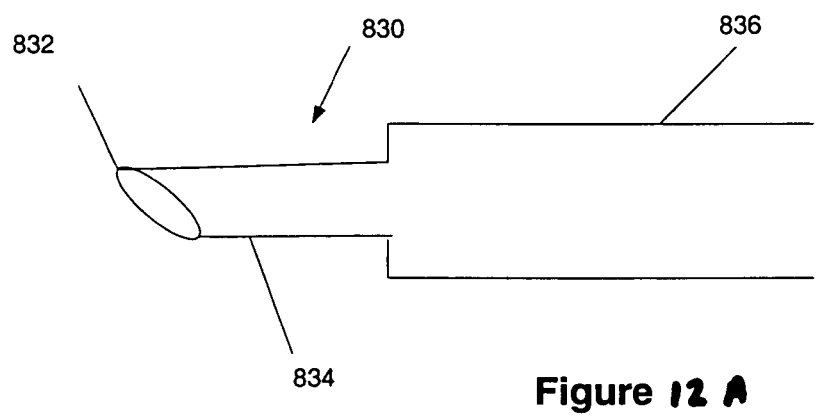
FIG. 12a illustrates an enlarged view of an alternative embodiment of a needle for use in the fluid delivery catheter shown in FIG. 10.
FIG. 12b illustrates an enlarged view of an alternative embodiment of a force transducer for use in the fluid delivery catheter shown in FIG. 10.
FIG. 12c illustrates an enlarged view of the needle of FIG. 9a and the force transducer of FIG. 12b.

FIG. 12A illustrates an enlarged view of an alternative embodiment of a needle 830 used in the fluid delivery catheter shown in FIG. 10. Here, the needle 830 has a stepped design with a distal (first) portion 834 and a proximal (second) portion 836. The needle tip is 832 is located on the distal portion 834. The distal portion 834 has a smaller diameter than the proximal portion 836. In one embodiment, the distal portion 832 has an outer diameter of 0.008 to 0.26 inches.

Figure 12B:
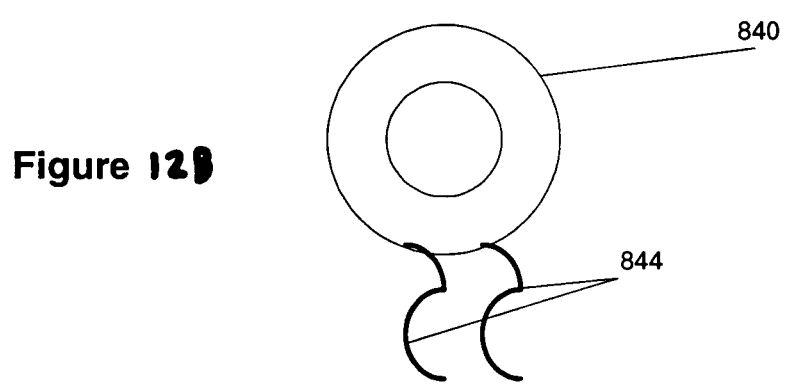
Figure 12C:
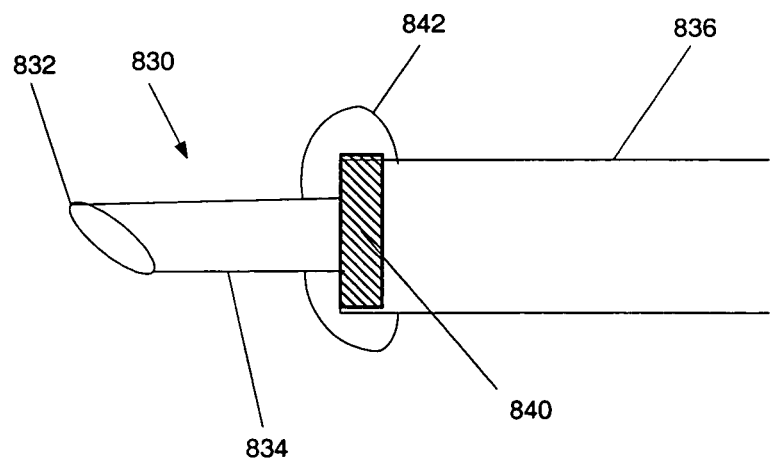

FIG. 12B illustrates an enlarged view of an alternative embodiment of a piezoelectric transducer 840 for use in the fluid delivery catheter as shown in FIG. 10. The piezoelectric transducer 840 is shown with leads 844. This piezoelectric transducer 840 is also seen in conjunction with the needle 830 in FIG. 12C. As seen in FIG. 12C, the piezoelectric transducer 840 is located on the stepped portion of the needle between distal portion 834 and the proximal portion 836 of the needle 830. The encapsulant 842 is located around the piezoelectric transducer 840. The stepped needle design is not necessary but may help to support the piezoelectric transducer 840 and improve manufacturability.

In one embodiment, the distal portion 834 of the needle 830 may have an outer diameter of 0.008 to 0.26 inches and a proximal portion diameter of 0.012 to 0.3 inches. In alternative embodiments, these dimensions may change according to application.

Figure 13:
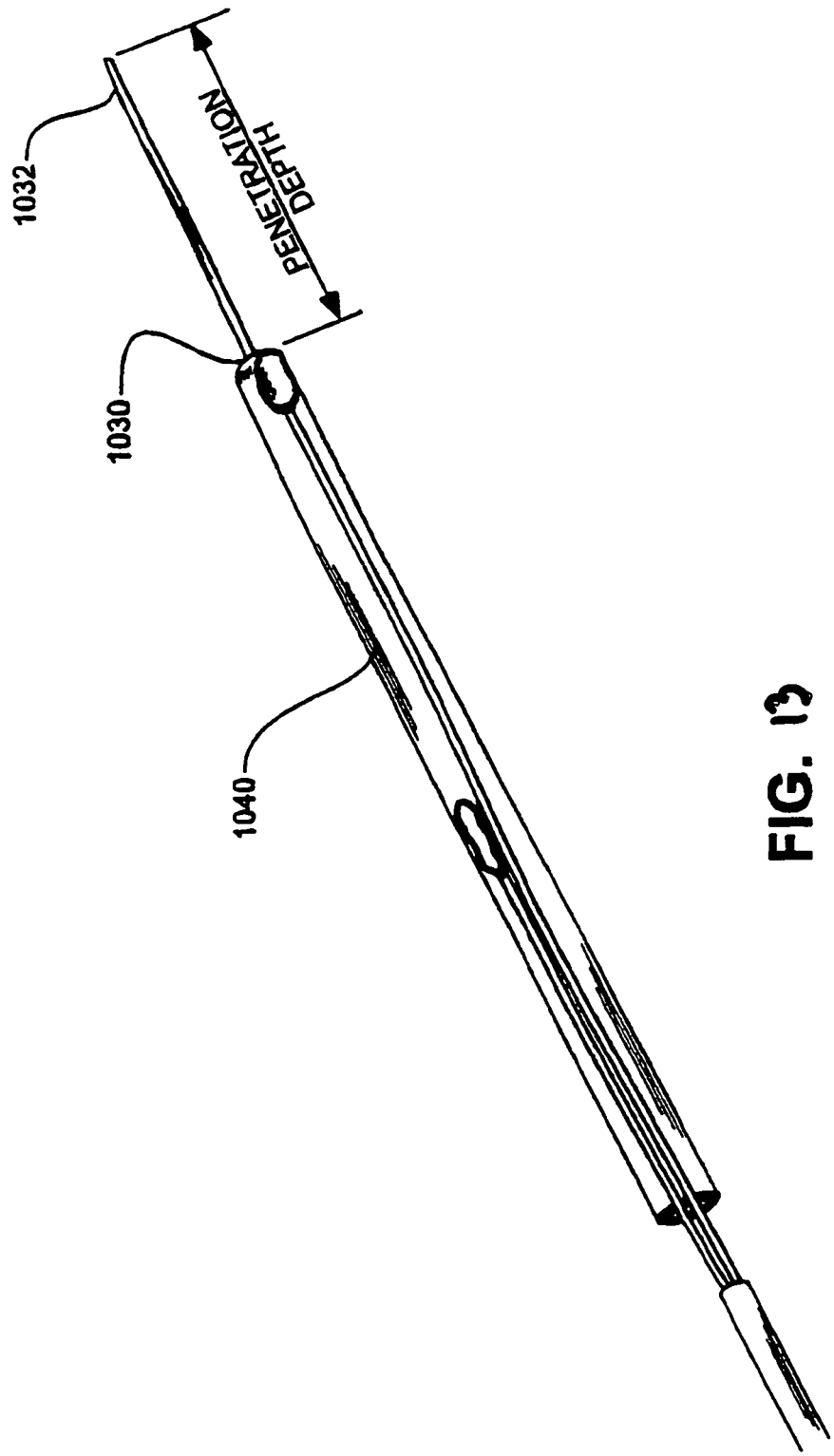
FIG. 13 illustrates a front view of one embodiment of a piezoelectric force transducer connected to the second end of a needle.

FIG. 13 illustrates a side view of one embodiment of a piezoelectric transducer with a tubular shape 1040 connected to the needle 1030. The piezoelectric transducer 1040 is located a predetermined distance from the needle tip 1032 so that an operator may detect when the needle 1030 has reached the desired penetration depth in the tissue.

In one embodiment the piezoelectric transducer 1040 may also be covered by a soft encapsulant material as was shown for the strain gauge discussed above in reference to FIGS. 10-12. In an alternative embodiment, the piezoelectric transducer may not be covered by the encapsulant material.

Figure 14:
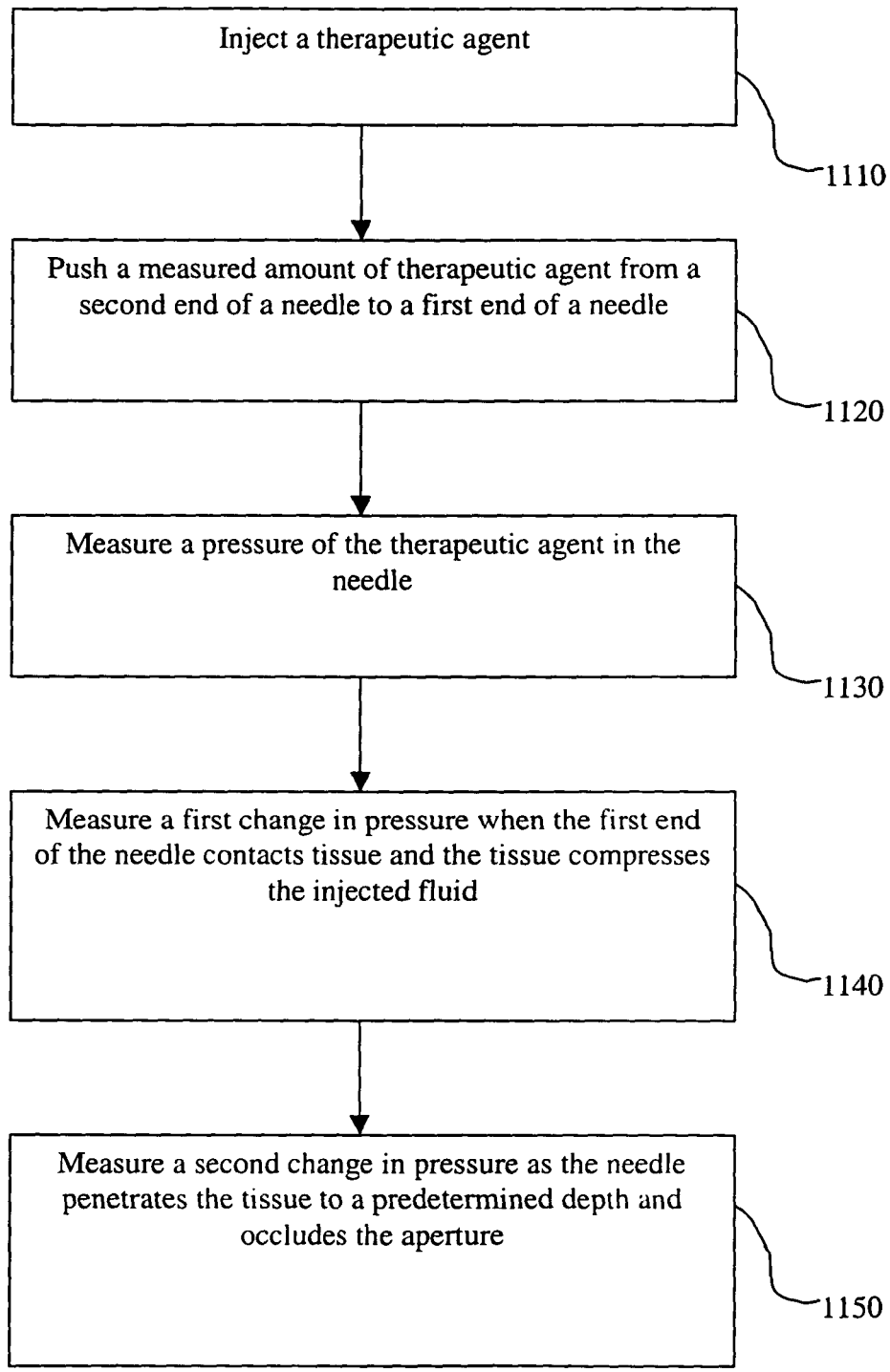
FIG. 14 illustrates a flow diagram of one embodiment of a process for detecting tissue contact and needle penetration depth.

FIG. 14 illustrates the flow chart of one embodiment of a process 1100 of detecting tissue contact and needle penetration depth. At processing block 1110 the syringe dispenses a therapeutic agent through the needle.

At processing block 1120, the needle dispenses a measured amount of therapeutic agent from a second end of a needle to a first end of the needle. At processing block 1130, the dynamic injection pressure of the therapeutic agent in the needle is measured. At processing block 1140, a first increase in the dynamic injection pressure is measured when the first end of the needle contacts tissue. At processing block 1150, a second increase in the dynamic injection pressure is measured as the needle penetrates into the tissue to a predetermined depth.

Figure 15:
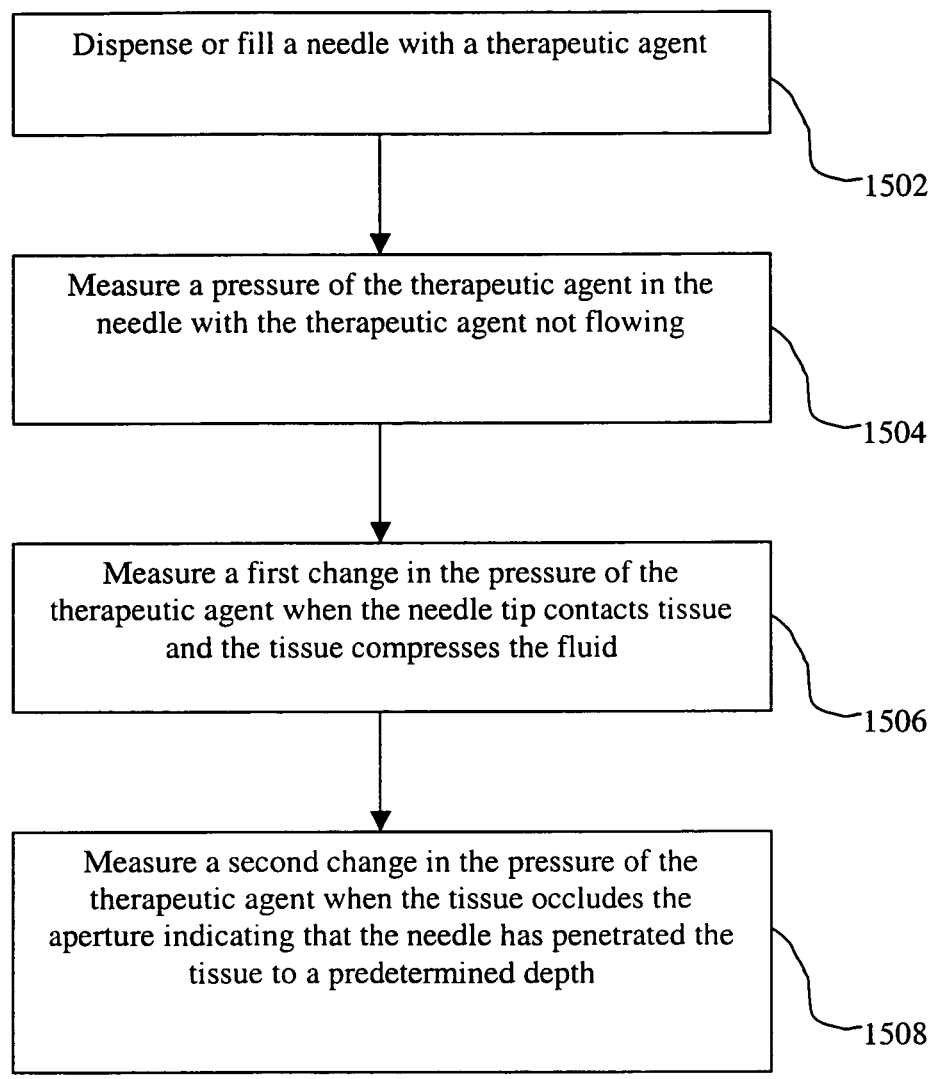
FIG. 15 illustrates another flow diagram of one embodiment of a process for detecting tissue contact and needle penetration depth.

FIG. 15 illustrates the flow chart of one embodiment of a process 1500 of detecting tissue contact and needle penetration depth. At processing block 1502 the syringe dispenses a therapeutic agent into the needle. Once the therapeutic agent has filled the needle, the therapeutic agent is not dispensed continuously as the needle is inserted into the tissue.

At processing block 1504, an initial static pressure of the therapeutic agent is measured with the therapeutic agent not flowing through the needle at this point. At processing block 1506, a first change in the static pressure of the therapeutic agent is measured when the needle tip lumen contacts and becomes occluded by the tissue. At processing block 1508, a second change in the pressure of the therapeutic agent is measured when the needle aperture becomes occluded as the needle penetrates the tissue to a predetermined depth.

Systems and methods for detecting tissue contact and needle penetration depth have been described. Although the present invention has been described with reference to specific exemplary embodiments, it will be evident that various modifications and changes may be made to these embodiments without departing from the scope of the invention. Accordingly, the specification and drawings are to be regarded in an illustrative rather than a restrictive sense.

What is claimed is:

1. A system for detecting tissue contact and penetration depth comprising:
   a needle with a first opening to and in fluid communication with a lumen of the needle and a second opening to and in fluid communication with the same lumen of the needle, said needle having the lumen extending between the first opening and the second opening, and the second opening including at least one aperture in the needle to the lumen located a predetermined distance from said first opening;
   a fluid pressure measurement assembly coupled with a portion of said needle to measure pressure of a fluid dispensed in said needle, said pressure measurement assembly configured to measure no significant change in pressure as compared to a first pressure that is the pressure of said fluid as said fluid is dispensed through said needle at a constant rate, a second pressure that is a significant increase in pressure as compared to the first pressure when said needle contacts said tissue and said first opening becomes occluded, and a third pressure that is a significant increase in pressure as compared to the second pressure when said needle penetrates said tissue and said aperture becomes occluded.

2. The system of claim 1 wherein said pressure measurement assembly comprises:
   a fluid pressure sensor.

3. The system of claim 1 wherein said pressure of fluid includes a pressure of a therapeutic agent to be injected into said tissue.

4. The system of claim 1 wherein said aperture has an area in said range between about 0.003 and 10 mm$^2$.

5. The system of claim 4 wherein said predetermined distance from said first end is about 0.5 to 10 millimeters.

6. The system of claim 1 wherein said predetermined distance is a desired penetration depth of said needle into said tissue.

7. The system of claim 1 wherein said first end of said needle has at least one of a tapered and untapered portion.

8. The system of claim 1 wherein said needle has an outer diameter in said range between about 0.008 and 0.26 inches.

9. The system of claim 1 wherein said needle has an inner diameter in said range between about 0.004 and 0.22 inches.

10. The system of claim 1 further comprises a computer processor coupling to said fluid pressure measurement assembly, said computer processor configured to perform at least one of determining and distinguishing said rate of changes in said static pressure to determine and distinguish said various penetration depths of said needle.

11. The system of claim 10 wherein said computer processor further couples to at least one of a visual feedback system indicator and an audible feedback system to issue human-recognizable signals as to penetration depths of said needle.

12. The system of claim 1 further comprising a signal processor or a computer processor coupled to the fluid pressure measurement assembly to differentiate the third pressure from the first pressure and from the second pressure by detecting the second pressure change when said needle penetrates said tissue said predetermined distance and said aperture becomes occluded.

13. The system of claim 1 further comprising a circuit to differentiate between: (1) a first pressure indicating that the needle has not reached the tissue; (2) a second pressure indicating that the needle has penetrated the tissue and the first opening has become occluded based on a change in pressure or a rate of change in pressure to a significantly larger magnitude; and (3) a third pressure indicating that the needle has penetrated the tissue by the predetermined distance and that the aperture is occluded based on a change in pressure or a rate of change in pressure to a significantly larger magnitude.

14. The system of claim 13 further comprising:
a visual indicator or an audible feedback system to indicate that the needle has not reached the tissue when the first pressure is measured;
to indicate that the needle has penetrated the tissue and the first opening has become occluded when the second pressure is measured; and
to indicate that the needle has penetrated the tissue by the predetermined distance when the third pressure is measured.

15. The system of claim 13 wherein the first opening is in a tip of the needle.

16. The system of claim 1 further comprising a visual indicator or an audio feedback system that indicates to an operator:
(1) to advance the needle in response to the fluid pressure measurement assembly measuring no significant change in pressure as compared to the first pressure, (2) to proceed with the advancement of the needle slowly in response to the fluid pressure measurement assembly measuring the significant increase in pressure as compared to the first pressure, and (3) to stop the advancement of the needle because the penetration depth desired has been achieved in response to the fluid pressure measurement assembly measuring the significant increase in pressure as compared to the second pressure.

* * * * *